Dec. 3, 1935. M H HORVATH Plant Pat. 152
ROSE
Filed April 26, 1935
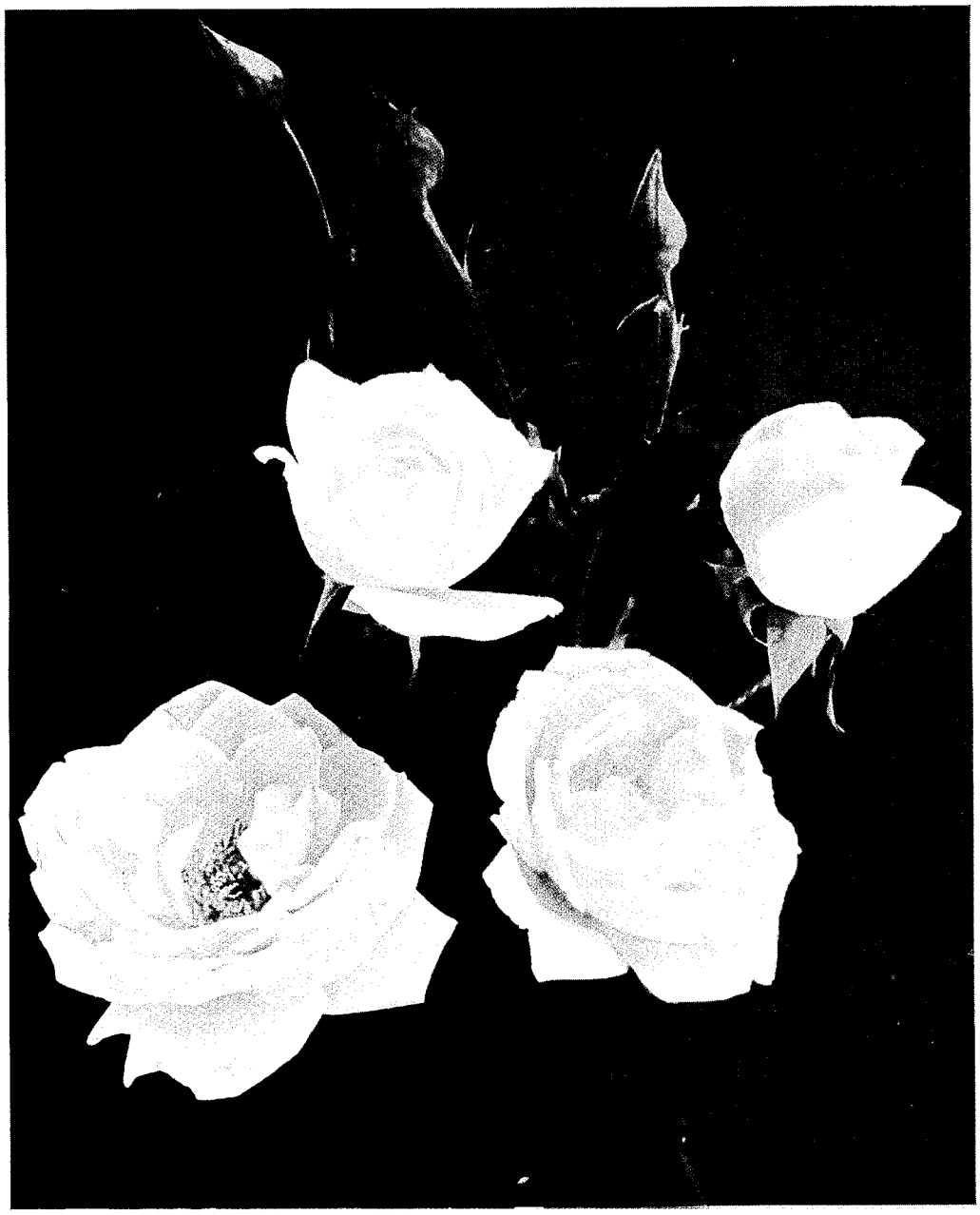
Inventor
M. H. Horvath
By Robb & Robb
Attorneys Patented Dec. 3, 1935

UNITED STATES PATENT OFFICE

152

ROSE

Michael H. Horvath, Mentor, Ohio, assignor to Jackson & Perkins Company, Newark, N. Y.

Application April 26, 1935, Serial No. 18,437

1 Claim. (Cl. 47—61)

The present invention relates to a new and distinct variety of rose plant and has for its main object the production from a new strain of a truly American hybrid variety of climber by breeding the native species rose Setigera (Prairie Rose) with the Austrian Briar, said new rose having greater winter hardiness than existing types, and novel bloom characteristics of great attraction.

In reference to its hardiness characteristics, this new variety has been found to survive lower temperatures than any of the known Wichuraiana hybrids or so-called hardy climbers.

As regards its bloom characteristics, it is notable that while retaining the native hardiness and blooming habit of its ancestors, in its interbreeding, it has acquired the form and quality of the hybrid tea. It is an extremely prolific bloomer, an established plant being fairly covered with yellow blooms to the extent of almost hiding the foliage, departing, of course, in color from that of either of its parents and thereby presenting another important feature of novelty.

But importantly, a still further essentially novel characteristic of this new variety resides in the habit of blooming twice in the same season, for about six weeks after its first blooming period has passed, a new abundant crop of bloom appears, lasting several weeks.

The novelty and distinctiveness of this new variety may thus be summarized to exist in the following characteristics, each of which is believed to be independently significant among hybrid climbers:

1. Greater hardiness.
2. Abundance of flowering.
3. Distinctive color of blooms.
4. Habit of blooming twice per season.

Asexual reproduction has shown these characteristics to be fixed.

It may also be noted that this new variety has been awarded the long standing "Replica of Feast Medal", offered for the best development of Rosa Setigera.

The following is a detailed description of this new variety:

Parentage:
Seedling.
*Seed parent.*—Rosa Setigera.
*Pollen parent.*—Rosa Fetida Bicolor Hybrid.

Classification:
*Botanic and commercial.*—Rosa Setigera Hybrid.

*Flower*

Blooming habit:
*Recurrent.*—Intermittent, spring and summer.

Bud:
*Size.*—Medium.
*Form.*—Short with flat top, ovoid. Unaffected by wet or hot weather.
**Color.*—When sepals first divide yellow with carmine markings. When petals begin to unfurl yellow. When half blown inside of petals yellow; reverse of petals yellow.
*Sepals.*—Smooth edge; stand up.
*Calyx.*—Shape funnel, size large, aspect smooth, odor when rubbed none.
*Peduncle.*—Length medium, aspect rough, color medium reddish brown strength erect, heavy.
*Opening.*—Opens well and is not affected by adverse conditions.

Bloom:
*Size.*—Large. Average size when fully expanded about 3½″.
*Borne.*—Several together, in clusters.
*Stems.*—Medium, strong.
*Form.*—When first opened cupped, globular.
*Permanence.*—Retains its form to the end.
*Petalage.*—Double (full but open center). Number of petals under normal conditions 20 to 25.
**Color.*—Center of flower yellow, outer petals yellow, base of petals (aiglet) yellow, inside of petals deeper yellow, reverse of petals lighter yellow, general tonality at a distance gold yellow.
*Variegations.*—None.
*Discoloration.*—General tonality at end of first day as above described. Second day fades slightly and third day turns toward cream according to weather.

Petals:
*Texture.*—Thick. Unaffected by wet or hot weather.
*Appearance.*—Inside satiny; outside satiny.
*Form.*—Round.
*Arrangement.*—Imbricated (regularly arranged shinglelike).
*Persistence.*—Drop off cleanly.
*Fragrance.*—Slight in nature of wildrose.
*Lasting quality.*—On the plant long, as cut flower fair.

Genital organs:
*Stamens, anthers.*—Large, many. Color—yellow. Arrangement—regular around styles.
*Stamens, filaments (threads).*—Long. Color—white.
*Pollen.*—Lemon yellow.
*Styles.*—Columnar, loosely separated, uneven length, medium, heavy.
*Stigmas.*—Color yellow.
*Ovaries.*—All enclosed in calyx.

Fruit:
Variety is fertile.
*Form.*—Round.

*Color nomenclature herein refers to Gravereaux color system)

*Aspect.*—Smooth.
*Color at maturity.*—Russet brown.
*Sepals.*—Caducous (soon falling).

*Plant*

Form:
Climber.
Growth:
Very vigorous.
Foliage:
Five, sometimes seven leaflets.
*Size.*—Large.
*Quantity.*—Abundant.
*Color.*—New foliage upper side light green; underside light glandular. Old foliage upper side dark green; underside light green.
*Shape.*—Oval pointed.
*Texture.*—Upper side leathery, glossy; underside velvety. Ribs and veins ordinary.
*Edge.*—Serrated (saw toothed).
*Serration.*—Single, large.
*Leaf stem.*—Color green. Underside prickles.
*Stipules.*—Long; smooth.
*Disease resistance.*—Susceptible to black spot.
Wood:
*New wood.*—Color light reddish brown. Bark—smooth.
*Old wood.*—Color reddish brown. Bark—smooth.
Thorns: (considering this to be divided into thorns, prickles and short needles)
*Thorns.*—Quantity—on main stalks from base ordinary. On laterals from stalk few. Form—broad base. Color when young green. Position—irregular.
*Prickles.*—Quantity—on laterals none.
*Short needles.*—Quantity—on main stalks none. On laterals none.

I claim:

A new and distinct variety of rose plant of a new strain, characterized by the great hardiness of the plant, its habit of prolifically blooming twice per season, as described, and the color of its blossoms, as shown.

MICHAEL H. HORVATH.